United States Patent
Di Giacomo et al.

(10) Patent No.: US 11,953,486 B2
(45) Date of Patent: Apr. 9, 2024

(54) TOTAL ORGANIC CARBON SENSOR UTILIZING DOWN CONVERSION

(71) Applicant: SENSIRION AG, Stäfa (CH)

(72) Inventors: Raffaele Di Giacomo, Stäfa (CH); Matthias Streiff, Stäfa (CH); Michael Merz, Stäfa (CH); Nicolas Moeller, Stäfa (CH)

(73) Assignee: SENSIRION AG, Zurich (CH)

( * ) Notice: Subject to any disclaimer, the term of this patent is extended or adjusted under 35 U.S.C. 154(b) by 68 days.

(21) Appl. No.: 17/628,229

(22) PCT Filed: Jul. 19, 2020

(86) PCT No.: PCT/EP2020/070396
§ 371 (c)(1),
(2) Date: Jan. 19, 2022

(87) PCT Pub. No.: WO2021/013774
PCT Pub. Date: Jan. 28, 2021

(65) Prior Publication Data
US 2022/0252570 A1    Aug. 11, 2022

(30) Foreign Application Priority Data
Jul. 19, 2019   (EP) .................................... 19187391

(51) Int. Cl.
*G01N 33/18* (2006.01)
*G01N 21/03* (2006.01)
(Continued)

(52) U.S. Cl.
CPC ......... *G01N 33/1846* (2013.01); *G01N 21/03* (2013.01); *G01N 21/33* (2013.01); *G01N 21/35* (2013.01); *G01N 2201/0668* (2013.01)

(58) Field of Classification Search
CPC .... G01N 33/1846; G01N 21/03; G01N 21/33; G01N 21/35
(Continued)

(56) References Cited

U.S. PATENT DOCUMENTS 3,958,942 A * 5/1976 Brazhnikov ........... G01N 21/33
422/98
4,632,807 A * 12/1986 Marsoner ............. G01N 21/274
422/91
(Continued)

FOREIGN PATENT DOCUMENTS

| CN | 105181602 | 12/2015 |
|---|---|---|
| DE | 102017205974 | 10/2018 |
| WO | 2018024840 | 2/2018 |

OTHER PUBLICATIONS

Blouke, M. M. et al., Applied Optics 1980, 19, 3318-3321. (Year: 1980).*
(Continued)

*Primary Examiner* — Arlen Soderquist
(74) *Attorney, Agent, or Firm* — JMB Davis Ben-David (57) ABSTRACT

The present invention relates to a sensor (1) for sensing organic carbon in a liquid (L), comprising: a container (2) having an interior space (20) for receiving the liquid (L), a photodetector (3), and a light source (4) configured to emit ultraviolet light (5) so that the ultraviolet light (5) travels along an optical path (P) through liquid (L) residing in the interior space (20) and is absorbable by carbon bonds of organic molecules in the liquid (L). According to the present invention, the photodetector (3) is configured to detect light in the visible or infrared spectrum, and the sensor (1) comprises a down conversion material portion (22; 22*a*) arranged in the optical path, wherein the down conversion material portion (22; 22*a*) is configured to receive incoming ultraviolet light (5) emitted by the light source (4) and to
(Continued)

down convert received ultraviolet light (5) and to emit said down converted light (50) in the visible or infrared spectrum so that emitted down converted light (50) impinges on the photodetector (3).

26 Claims, 7 Drawing Sheets

(51) Int. Cl.
*G01N 21/33* (2006.01)
*G01N 21/35* (2014.01)

(58) Field of Classification Search
USPC .......................................................... 436/146
See application file for complete search history.

(56) References Cited

U.S. PATENT DOCUMENTS

| | | | | |
|---|---|---|---|---|
| 4,752,447 | A * | 6/1988 | Kimmel | G01N 21/783 356/402 |
| 4,775,794 | A * | 10/1988 | Behmann | G01N 21/33 250/435 |
| 5,039,490 | A * | 8/1991 | Marsoner | G01N 21/255 356/402 |
| 5,266,486 | A * | 11/1993 | Fraatz | G01N 21/77 435/165 |
| 5,517,313 | A * | 5/1996 | Colvin, Jr. | G01N 21/6428 356/417 |
| 5,894,351 | A * | 4/1999 | Colvin, Jr. | G01N 21/6428 356/417 |
| 6,340,824 | B1 * | 1/2002 | Komoto | H01L 33/507 257/89 |
| 6,389,048 | B2 | 5/2002 | Stamm et al. | |
| 8,742,370 | B2 * | 6/2014 | Tkachuk | G01N 21/77 250/458.1 |
| 2001/0040905 | A1 * | 11/2001 | Stamm | G01J 1/58 372/32 |
| 2003/0156290 | A1 * | 8/2003 | Colvin, Jr. | G01N 21/7703 356/417 |
| 2005/0148094 | A1 * | 7/2005 | Tyrrell | G01N 21/645 436/172 |
| 2006/0006339 | A1 | 1/2006 | Fraser et al. | |
| 2009/0268204 | A1 | 10/2009 | Tkachuk | |
| 2012/0080615 | A1 * | 4/2012 | Kingsley | C09K 11/06 257/E31.127 |
| 2013/0153777 | A1 | 6/2013 | Sexton et al. | |
| 2019/0181181 | A1 | 6/2019 | Yeon et al. | |
| 2019/0195787 | A1 | 6/2019 | Tröllsch | |

OTHER PUBLICATIONS

Ponomarenko, S. A. et al., SPIE 2015, paper 954509, 9 pages. (Year: 2015).*

Zou, T. et al., Advance Optical Materails 2019, 7, paper 1801812, 8 pages with 5 pages of supporting information. (Year: 2018).*

Zijun Wang et al., "Dye-Sensitized Downconversion", Journal of Physical Chemistry Letters, vol. 9, No. 7, Mar. 9, 2018 (Mar. 9, 2018), p. 1522-1526.

* cited by examiner

TOTAL ORGANIC CARBON SENSOR UTILIZING DOWN CONVERSION

CROSS-REFERENCE TO RELATED APPLICATIONS

This is the U.S. National Stage of International Patent Application No. PCT/EP2020/070396 filed Jul. 19, 2020, and which in turn claims the benefit of European Patent Application No. 19187391.8 filed Jul. 19, 2019.

The present invention relates to a sensor for sensing carbon bonds of organic molecules in a liquid, particularly water, based on ultraviolet (UV) light.

Such sensors are particularly used to sense the so-called total organic carbon (TOC), dissolved organic carbon (DOC), the water quality test parameter UV254 and/or chemical oxygen demand (COD).

The total organic carbon (TOC) value is a sum parameter frequently used in environmental analysis and indicates the sum of the total organic carbon in a sample. This parameter is often presented as mass per volume in (e.g. mg/L). It is thus a measure for the content of organic carbon in an e.g. liquid probe such as water. The TOC therefore excludes inorganically bound carbon, such as carbonates or $CO_2$.

Organic carbon content in a liquid correlates with the UV absorbance of the liquid.

US2016/0356713A1 discloses an inline water contaminant detector comprising a photometric sensor for detecting absorption of ultraviolet light that is generated with a UV254 LED that can be activated when water fills a sample chamber of the detector.

However, due to the use of electronic components such as photodetectors sensitive in the ultraviolet region of the light spectrum such sensors are relatively expensive.

The problem to be solved by the present invention is therefore to provide a sensor that comprises a simple and cost effective design that allows to sense organic carbon, particularly TOC, DOC, UV254 and/or COD, in a liquid.

This problem is solved by a sensor having the features of the claims herein. Preferred embodiments of the sensor are stated in the sub claims and are stated below. According to the claims herein, a sensor for sensing organic carbon, particularly TOC, DOC, UV254 and/or COD, in a liquid (particularly water) is disclosed, the sensor comprising:
- a container having an interior space for receiving the liquid,
- a photodetector,
- a light source configured to emit ultraviolet light so that the ultraviolet light travels along an optical path through liquid residing in the interior space and is absorbable by carbon bonds of organic molecules in the liquid.

In the framework of the present invention, a carbon bond is a carbon-carbon bond, i.e., a covalent bond between two carbon atoms.

According to the present invention, the photodetector is configured to detect light in the visible or infrared spectrum, and the sensor comprises a down conversion material portion arranged in the optical path, wherein the down conversion material portion is configured to receive incoming ultraviolet light emitted by the light source and to down convert received ultraviolet light and to emit said down converted light in the visible or infrared spectrum so that emitted down converted light impinges on the photodetector.

Advantageously, due to using a down conversion material that converts ultraviolet radiation into light in the visible or infrared spectrum, a dedicated ultraviolet light photodetector/photodiode can be omitted.

Particularly, ultraviolet (UV) light is light comprising a wavelength between 100 nm and 400 nm and thus particularly has a shorter wavelength than the visible violet light. Furthermore, infrared (IR) light lies just beyond the red end of the visible spectrum. The UV portion of the spectrum is divided into three regions: UVA (315 nm to 400 nm), UVB (280 nm to 315 nm) and UVC (100 nm to 280 nm).

Furthermore, the present invention allows to use a larger photodetector and thus generates a higher resolution without increasing costs.

Particularly, due to specific design, the sensor according to the present invention is more robust regarding bubbles being present in the liquid to be tested.

Furthermore, using a reflective surface/down conversion material facing the light source/photodetector more light can be collected which also increases the resolution of the sensor.

According to an embodiment of the present invention, the light source is a light emitting diode (LED) configured to emit UV light. Furthermore, in an embodiment, the photodetector is a photodiode that is sensitive in the visible or infrared spectrum. Particularly, the photodetector/photodiode can be based on materials such as Si, GaAs (VIS-NIR, IR) and the light source/LED can be based on materials such as GaN, SiC.

Further, according to a preferred embodiment, said optical path, along which UV light can be absorbed in the liquid by carbon bonds of organic molecules, comprises a length of 1 cm to 10 cm, particularly 2 cm to 6 cm.

Furthermore, according to an embodiment of the present invention, the container comprises an interior surface facing the interior space of the container.

Preferably, the interior surface comprises one of: a flat region, a curved region, a concave region, a parabolic region, an ellipsoidal region.

Further, in an embodiment, at least a region of said interior surface (particularly the complete interior surface or said flat, curved, concave, ellipsoidal or parabolic region) is formed by said down conversion material portion, particularly such that ultraviolet light emitted by the light source impinges on said down conversion material portion and down converted light emitted by said down conversion material portion impinges on the photodetector.

Furthermore, according to an embodiment of the present invention, said down conversion material portion forms a layer with a thickness of 100 nm to 5 mm arranged on the photodetector, particularly such that ultraviolet light emitted by the light source impinges on said interior surface (e.g. on said flat, concave, ellipsoidal or parabolic region), is reflected by the interior surface, impinges on said layer and down converted light emitted by said layer impinges on the photodetector. Therefore, in case the down conversion material portions forms said layer arranged on the photodetector, said interior surface is designed to reflect ultraviolet light according to an embodiment. According to a further embodiment, said layer formed by the down conversion material portion comprises a thickness in the range from 100 nm to 5 mm, particularly in the range from 1 µm to 1 mm.

Furthermore, according to an embodiment of the present invention, the down conversion material forming the respective down conversion material portion is one of or comprises one of the following materials: a polystyrene, a fluorescent polymer, a fluorescent ceramics, semiconductor particles in the form of quantum dots embedded in a polymer matrix or in a glass matrix or in a film, an organic fluorophore, porcelain, terracotta, sandstone, a glass, PVC (polyvinyl chloride), a fluorescent polymer clay.

Furthermore, according to an embodiment, the down conversion material may contain one or more of the following additives:

a) An ultraviolet absorber (i.e. a material that absorbs ultraviolet light), preferably one of: rutile titanium oxide, titan dioxide, hydroxybenzophenone, hydroxybenzophenone oxanilide, hydroxyphenylbenzotriazole, hydroxyphenylbenzotriazole oxanilide, benzophenone, benzotriazole, hydroxyphenyltriazine.

b) A quencher, preferably a nickel quencher, to reduce the fluorescence in order to extend the lifetime of the down conversion material. Here, quenching refers to any process which decreases the fluorescence intensity of a given substance.

c) Hindered Amine Light Stabilizers (HALS), preferably 2,2,6,6-tetramethylpiperidine.

Furthermore, according to an embodiment of the present invention, the sensor comprises a lid connected to the container for closing the container.

Particularly, the lid comprises a first surface facing the interior space of the container, wherein preferably said first surface is opaque, i.e. non-translucent. Particularly, the surface can be black (e.g. coated with a black paint/material) or metallic. Furthermore, also an exterior surface of the container is preferably opaque.

Furthermore, according to an embodiment of the present invention, the sensor comprises a sealing member arranged between the lid and a face side of the container, which face side comprises an opening of the container that is closed by the lid.

Furthermore, according to an embodiment of the present invention, the container comprises a flange forming said face side, wherein the lid is connected to the flange.

Furthermore, according to an embodiment of the present invention, the photodetector and the light source are mounted to the lid outside said interior space of the container, particularly to a second surface of the lid that faces away from said first surface from the lid or from the interior space of the container.

Furthermore, according to an embodiment of the present invention, the photodetector and the light source are arranged on a printed circuit board that is mounted to the lid, particularly to said second surface of the lid, or wherein the photodetector is mounted to a first printed circuit board and the light source is mounted to a second printed circuit board, wherein the two printed circuit boards are mounted to the lid, particularly to said second surface of the lid.

Furthermore, according to an embodiment of the present invention, the lid comprises a first aperture to allow passage of light from the interior space towards the photodetector, and wherein the lid comprises a second aperture to allow passage of ultraviolet light emitted by the light source into the interior space of the container.

Particularly, in an embodiment, the photodetector is arranged outside the interior space of the container in front of the first aperture. Furthermore, particularly, the light source is arranged outside the interior space of the container in front of the second aperture.

Further, according to an embodiment, the first aperture is closed by a first optical window allowing passage of light therethrough, wherein the first optical window is configured to prevent liquid residing inside the interior space from leaking through the first aperture out of the interior space. Furthermore, in an embodiment, the second aperture is closed by a second optical window allowing passage of light therethrough, wherein the second optical window is configured to prevent liquid residing inside the interior space from leaking through the second aperture out of the interior space.

Furthermore, according to an embodiment of the present invention, the container comprises a protrusion protruding from an outside of a wall of the container, which wall delimits the interior space and comprises said interior surface, wherein said protrusion comprises an edge extending perpendicular to the lid of the container.

Furthermore, according to an embodiment of the present invention, the sensor comprises a conduit connected to the container, which conduit is configured to guide liquid into the container and out of the container, wherein the conduit is connected to a boundary portion of the container comprising the opening of the container that is closed by the lid.

Preferably, in an embodiment, the conduit is connected to said flange and/or an outside of the wall of the container. Particularly, the conduit can be formed by a tube comprising a lateral opening that is in fluid communication with the interior space of the container. Further, according to an embodiment, the tube or conduit comprises an inlet at one end of the tube/conduit and an outlet at an opposing end of the tube/conduit, so that liquid can be passed into the interior space of the container via the inlet and the lateral opening and can be discharged out of the interior space of the container via the lateral opening and the outlet of the tube/conduit.

According to an alternative embodiment, the conduit can also be connected to the lid of the container.

Furthermore, according to an embodiment of the present invention, the sensor comprises an analyzing circuit. Particularly, the analyzing circuit is configured to analyze an output signal of the photodetector and to generate an output indicative of a concentration of organic carbon in said liquid. Particularly, said concentration refers to a mass per volume concentration. Other suitable measures are also conceivable.

Particularly, the output signal of the photodetector is an electrical current that is proportional to the intensity of the down converted light impinging on the photodetector. According to an alternative embodiment, the analyzing circuit can be arranged in or formed by an external device (e.g. a mobile device such as a smart phone). Such a system then comprises a sensor according to the present invention and an (e.g. external) analyzing circuit that is configured to receive data from the sensor (e.g. in a wireless fashion or via a cable).

Furthermore, according to an embodiment of the present invention, the sensor comprises a further light source configured to emit light in the visible spectrum such that the light is reflected by the down conversion material portion of the interior surface of the container, wherein the sensor is configured to measure the reflected light (which is not down-converted because it is visible light) to estimate a value indicative of at least one of: an aging of the down conversion material portion (due to ultraviolet light incident on the down conversion material portion, e.g. photo bleaching of the down conversion material portion due to ultraviolet light incident on the down conversion material portion), a contamination (e.g. scale, biofilm etc.) deposited on the down conversion material portion and/or on the first optical window and/or on the second optical window.

Furthermore, in an embodiment, the photodetector is used to measure said reflected visible light coming from the further light source. Alternatively, the sensor may comprise a further photodetector (e.g. a photo diode sensing in a visible spectrum) to measure the visible light coming from the further light source and reflected from the interior surface of the interior space of the container. Furthermore, the further light source can be arranged on said (single) printed circuit board or on the second printed circuit board. Particularly, the further light source is arranged adjacent the light source that emits the ultraviolet light.

Particularly, according to an embodiment, the analyzing circuit is configured to use said estimated value in the generation of said output to compensate an effect of at least one of said aging (e.g. bleaching) and contamination. Furthermore, the analyzing circuit can also be configured to use the visible light source to compensate for turbidity in the liquid.

Furthermore, according to an embodiment, the sensor comprises a further photodetector configured to detect light in the visible or infrared spectrum, and wherein the light source is further configured to also emit ultraviolet light that travels along a further optical path through the liquid and is absorbable by carbon bonds of organic molecules in the liquid, wherein the sensor comprises a further down conversion material portion arranged in the further optical path, wherein the further down conversion material portion is configured to receive incoming ultraviolet light emitted by the light source and to down convert received ultraviolet light and to emit said down converted light in the visible or infrared spectrum so that emitted down converted light impinges on the further photodetector, and wherein a length of the optical path differs from a length of the further optical path.

Particularly, according to an embodiment, the interior surface comprises a first region and a second region.

According to an embodiment, the first region is formed by the down conversion material portion and the second region is formed by the further down conversion material portion, such that ultraviolet light traveling along the optical path impinges on the first region of the interior surface and down converted light emitted by said first region of the interior surface impinges on the photodetector, and such that ultraviolet light traveling along the further optical path impinges on the second region of the interior surface and down converted light emitted by said second region of the interior surface impinges on the further photodetector.

According to an alternative embodiment, the down conversion material portion forms a layer (e.g. with a thickness of 100 nm to 5 mm, particularly 1 µm to 1 mm) arranged on the photodetector, particularly such that ultraviolet light emitted by the light source impinges on a first region of said interior surface, is reflected by the first region of the interior surface, impinges on said layer and down converted light emitted by said layer impinges on the photodetector, and wherein the sensor comprises a further down conversion material portion that forms a further layer arranged on the further photodetector, particularly such that ultraviolet light emitted by the light source impinges on a second region of said interior surface, is reflected by the second region of the interior surface, impinges on said further layer and down converted light emitted by said further layer impinges on the further photodetector.

According to a further embodiment, the sensor comprises a first optical window separating the photodetector from the interior space of the container. Furthermore, according to an embodiment, the sensor comprises a second optical window separating the further photodetector from the interior space of the container (yet another optical window, e.g. a third optical window, can separate the light source from the interior space of the container).

According to an embodiment, the down conversion material portion is comprised or formed by the first optical window separating the photodetector from the interior space of the container. Furthermore, according to an embodiment, the further down conversion material portion is comprised or formed by the second optical window separating the further photodetector from the interior space of the container.

Thus, particularly, ultraviolet light emitted by the light source impinges on the first region of said interior surface, is reflected by the first region of the interior surface and eventually impinges on said first optical window and down converted light emitted by said first optical window impinges on the photodetector. Likewise, particularly, ultraviolet light emitted by the light source impinges on the second region of said interior surface, is reflected by the second region of the interior surface and eventually impinges on said second optical window and down converted light emitted by said second optical window impinges on the further photodetector.

Furthermore, according to an embodiment of the present invention, the down conversion material forming the respective down conversion material portion is one of or comprises one of the following materials: a fluorescent mineral, ruby, willemite, fluorite, calcite, agrellite, apatite, aragonite, baryte, cerussite, chalcedony, corundum, esperite, hardystonite, hyalite, hydrozincite, opal, pyromorphite, scapolite, scheelite, selenite, smithsonite, sodalite, sphalerite, tremolite, tugtupite, wollastonite, caliche.

Furthermore, according to a preferred embodiment, the first and second optical window separating the respective photodetector from the interior space of the container are formed out of ruby.

Preferably, the first region of the interior surface is one of: a flat region, a curved region, a concave region, a parabolic region, an ellipsoidal region, a hemispherical region. Furthermore, the second region of the interior surface is one of: a flat region, a curved region, a concave region, a parabolic region, an ellipsoidal region, a hemispherical region.

Furthermore, according to an embodiment, the first region of the interior surface comprises a curvature having a radius that is larger than a radius of a curvature of the second region of the interior surface.

Furthermore, according to an embodiment, the first and the second region of the interior surface, particularly in case of hemispherical regions, intersect at an intersection such that for each of the two hemispheres, the respective radius pointing to the intersection and the respective radius perpendicular to the flat surface of the hemisphere (i.e. the radius pointing to the apex of the respective hemisphere/region) form an angle between 0° and 90°.

Furthermore, according to an embodiment, the photodetector faces the first region of the interior surface, the further photodetector faces the second region of the interior surface, and the light source faces said intersection.

Furthermore, according to an embodiment (in case the down conversion material portions are not formed by the first and second region of the interior surface), the first region of the interior surface and the second region of the interior surface each comprise a reflectance between 0.1 and 0.99, and are each configured to reflect light in a diffuse manner (diffuse reflection).

Furthermore, according to an embodiment, the first and the second region of the interior surface are configured to direct specular reflections of the light emitted by the light source away from said two windows. Particularly, the first and the second region of the interior surface are configured such that mainly diffuse reflected light is impinging on said two optical windows. This helps to avoid specular reflected light to go on the photodetectors, which is desirable because this type of reflection is the one changing the most with material aging.

According to yet another embodiment, the photodetector and the further photodetector are each configured to generate an output signal indicative of an intensity of the light impinging on the respective photodetector, wherein a ratio of the two output signals is indicative of a concentration of organic carbon in said liquid and independent of the total reflectance and the proportion between specular reflectance and diffuse reflectance. of the first and second region of the interior surface.

Particularly, the analyzing circuit is configured to determine said ratio in order to estimate said concentration of organic carbon.

Furthermore, according to an embodiment, the analyzing circuit is configured to analyze an output signal of the further photodetector and to generate a further output indicative of a concentration of organic carbon in said liquid. Particularly, the output signal of the further photodetector is an electrical current that is proportional to the intensity of the down converted light impinging on the further photodetector. Furthermore, particularly, the analyzing circuit is configured to use the output and the further output to calculate a concentration of organic carbon in said liquid that is independent of contamination (e.g. scale, biofilm, etc.) deposited on the interior surface and/or on the first optical window and/or on the second optical window and/or on the third optical window of the sensor.

Furthermore, according to an embodiment, the analyzing circuit is configured to analyze an output signal of the photodetector also when the sensor is emptied from liquid (e.g. water) and to use this value as a baseline for the measurements of TOC in water.

The reference value acquired without liquid (e.g. water) is indicative of at least one of: an aging of the down conversion material portion (due to ultraviolet light incident on the down conversion material portion, particularly photo bleaching of the down conversion material portion due to ultraviolet light incident on the down conversion material portion), a contamination (e.g. scale, biofilm etc.) deposited on the down conversion material portion.

In other words, according to an embodiment, the sensor can be configured such that the interior space can be emptied of liquid (e.g. water) and the analyzing circuit (e.g. processor) knows that (e.g. can detect such a state). The light on the photodetector in this case has not experienced absorption from the liquid (e.g. water) and thus it can be used as a baseline to cancel the effects of photobleaching of the down-conversion material (or deposits such as scale or biofilm).

According to an embodiment, the container comprises an orifice for discharging liquid (e.g. water) out of the interior space of the container of the sensor. Particularly, this orifice allows liquid (e.g. water) to flow out of the interior space of the sensor (e.g. into a water pipe) by which air can enter the sensor.

Yet another aspect of the present invention relates to a sensor corresponding to the sensor according to the present invention, wherein here the down conversion material portion(s) are omitted and the photodetectors are configured to detect UV light. Such an omission of down conversion material portion(s) and replacing of the respective photodetector with an ultraviolet light photodetector can be applied to all embodiments described herein.

According to a preferred embodiment, such a sensor, for sensing carbon bonds of organic molecules in a liquid (e.g. water), comprises:
  a container having an interior space for receiving the liquid,
  a light source configured to emit ultraviolet light so that the ultraviolet light travels along an optical path through liquid residing in the interior space and is absorbable by carbon bonds of organic molecules in the liquid, and
  a photodetector and a further photodetector, each configured to detect ultraviolet (UV) light emitted by the light source.

This sensor can be further specified by the features described herein with regard to the corresponding sensor comprising down conversion material portion(s).

In the following, preferred embodiments of the present invention as well as further features and advantages of the present invention are described with reference to the Figures, wherein

Figure 1:
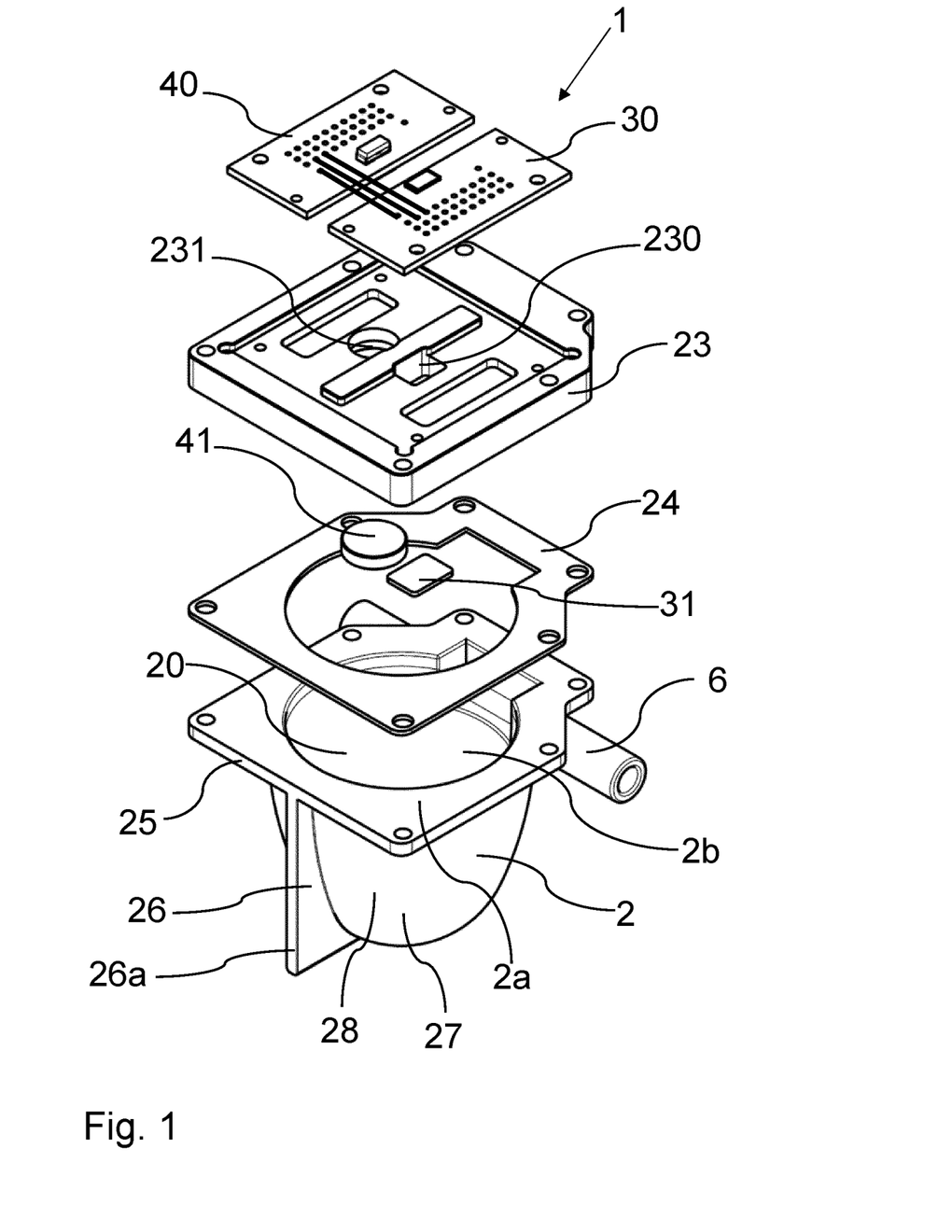
FIG. 1 shows an exploded view of an embodiment of a sensor according to the present invention.

FIG. 1 shows in conjunction with FIGS. 2 to 8 an embodiment of a sensor 1 for measuring a concentration of organic carbon in a liquid L, e.g. water, wherein the sensor 1 is particularly adapted to measure TOC (total organic carbon).

To this end, the sensor 1 comprises a container 2 delimiting an interior space 20 for accommodating an amount of liquid L to be analyzed with respect to organic carbon, a photodetector 3, and a light source 4 configured to emit ultraviolet light 5 so that the ultraviolet light 5 travels along an optical path through liquid L residing in the interior space 20 and is absorbable by organic carbon (particularly carbon bonds) in the liquid L.

Figure 6:
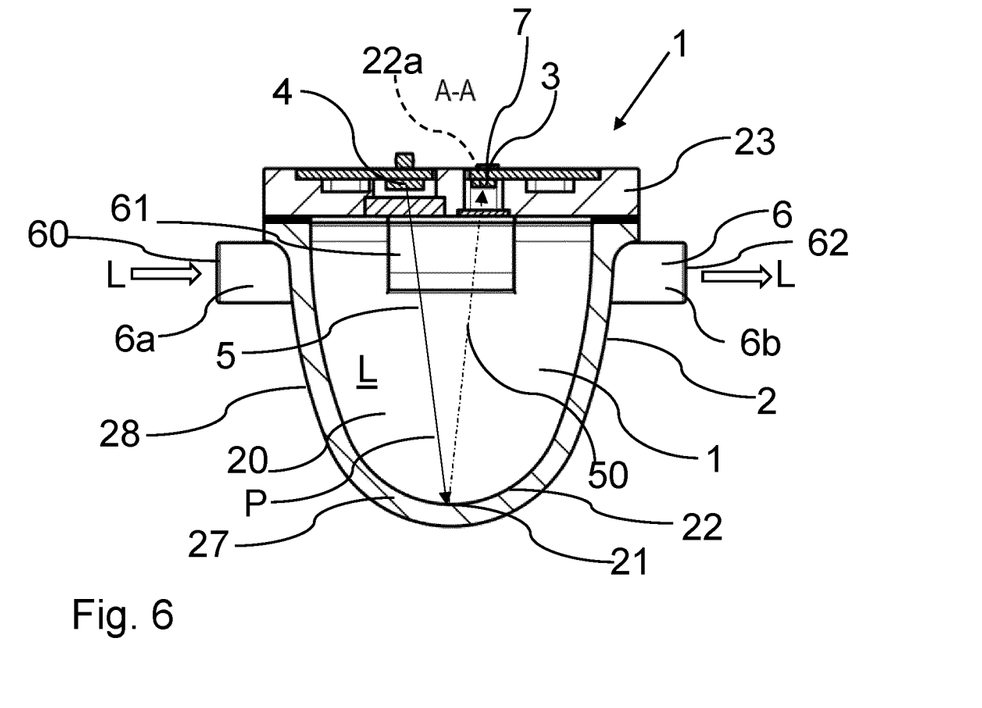
FIG. 6 shows a cross sectional view of the sensor shown in FIGS. 1 to 5 along the line A-A in FIG. 5.

According to the present invention, the photodetector 3 is configured to detect light in the visible or infrared spectrum, and the sensor 1 comprises a down conversion material portion 22 arranged in the optical path (cf. e.g. FIG. 6), wherein the down conversion material portion 22 is configured to receive incoming ultraviolet light 5 emitted by the light source and to down convert received ultraviolet light 5 and to emit said down converted light 50 in the visible or infrared spectrum so that emitted down converted light 50 impinges on the photodetector 3 (cf. FIG. 6).

Said visible or infrared light emitted from the down converting material portion 22 and traveling through the liquid L (e.g. water) is not absorbed by organic carbon bonds due to its longer wavelength (compared to the UV light).

Preferably, the light source 4 is formed by a light emitting diode (LED) and the photodetector 3 preferably is a photodiode that is sensitive in the visible or infrared spectrum.

As particularly indicated in FIG. 6, the container 2 comprises an interior surface 21 facing the interior space 20 of the container 2. Particularly, the interior surface 21 comprises a concave shape, particularly a parabolic curvature.

Preferably, in order to down convert UV light 5 to visible/IR light 50 that can be sensed by the photodetector 3, at least a region of said interior surface 21 (particularly the complete interior surface 21 or a curved, concave or parabolic region) is formed by said down conversion material portion 22. Hence, ultraviolet light 5 emitted by the light source 4 impinges on said down conversion material portion 22 and down converted light 50 emitted by said down conversion material portion 22 impinges on the photodetector 3.

Alternatively, as also indicated in FIG. 6 by means of a dashed line, said down conversion material portion may also form a layer 22a arranged on the photodetector 3 instead. Then, ultraviolet light 5 emitted by the light source 4 impinges on said interior surface 21 which is now not formed out of a down conversion material, but comprises a reflective surface (e.g. a metal such as aluminum) so that the UV light 5 is reflected by the interior surface 21, and reflected UV light 50 impinges on said layer 22a, is down converted by said layer 22a, and eventually impinges on the photodetector 3 (as visible or infrared light).

Particularly, said optical path P comprises a length of 1 cm to 10 cm, particularly 4 cm to 6 cm.

Particularly, the down conversion material can be a fluorescent polymer or ceramics. Other materials may also be used. Particularly, the entire container 2/wall 27 of the container may be formed out of the down conversion material and may thus form said portion 22. Alternatively, the interior surface 21 can be formed by a coating or layer arranged on the wall 27 of the container 2 so that the coating/layer forms the down conversion material portion 22.

In order to close an opening 2b of the container 2 on a face side 2a of the container 2, the sensor 1 comprises a lid 23 connected to the container 2. Particularly, the lid 23 comprises a first surface 23a facing the interior space 20/face 2a of the container 2 (cf. e.g. FIG. 2), wherein preferably said first surface 23a is opaque (non-translucent), e.g. black, so that preferably light cannot be transmitted through the surface 23a. In order to seal a connection between the lid 23 and said face side 2a of the container 2, a circumferential sealing member 24 is placed between the lid 23 and the face side 2a.

Particularly, the container 2 comprises a flange 25 forming said face side 2a, wherein the lid 23 is connected to the flange 25 (e.g. using bolts and nuts).

Figure 2:
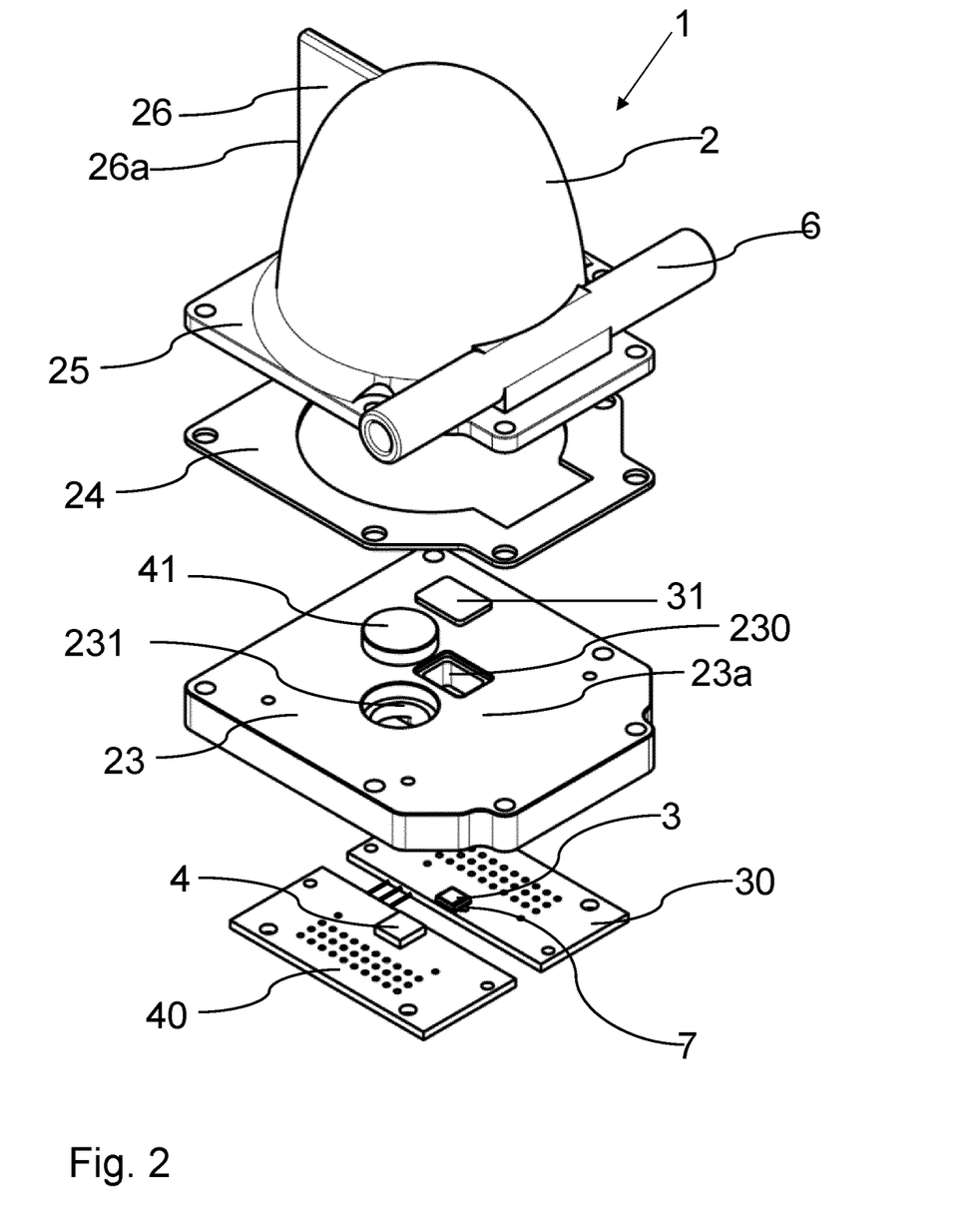
FIG. 2 shows a further exploded view of the sensor shown in FIG. 1.
Figure 3:
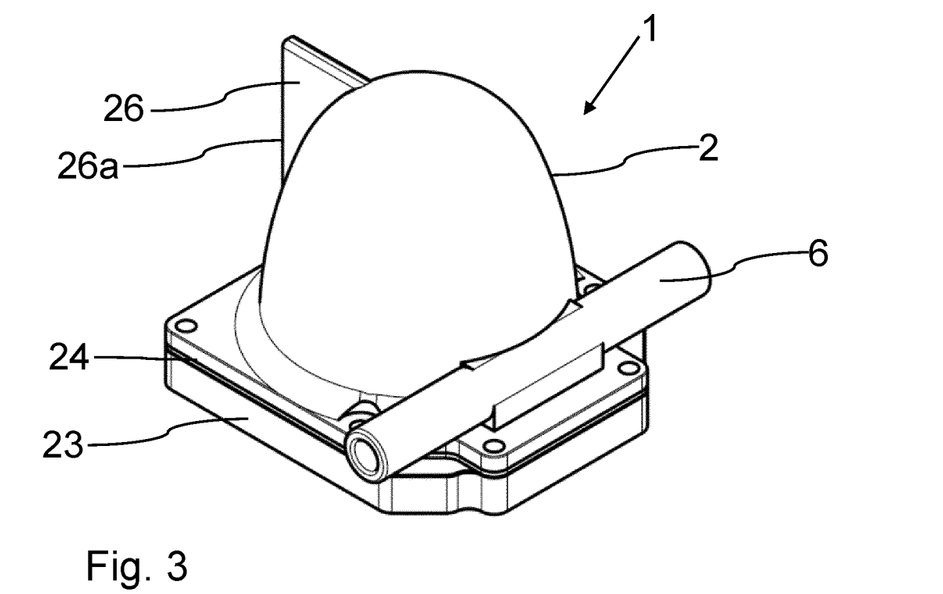
FIG. 3 shows a perspective view onto the container of the sensor shown in FIGS. 1 and 2.
Figure 4:
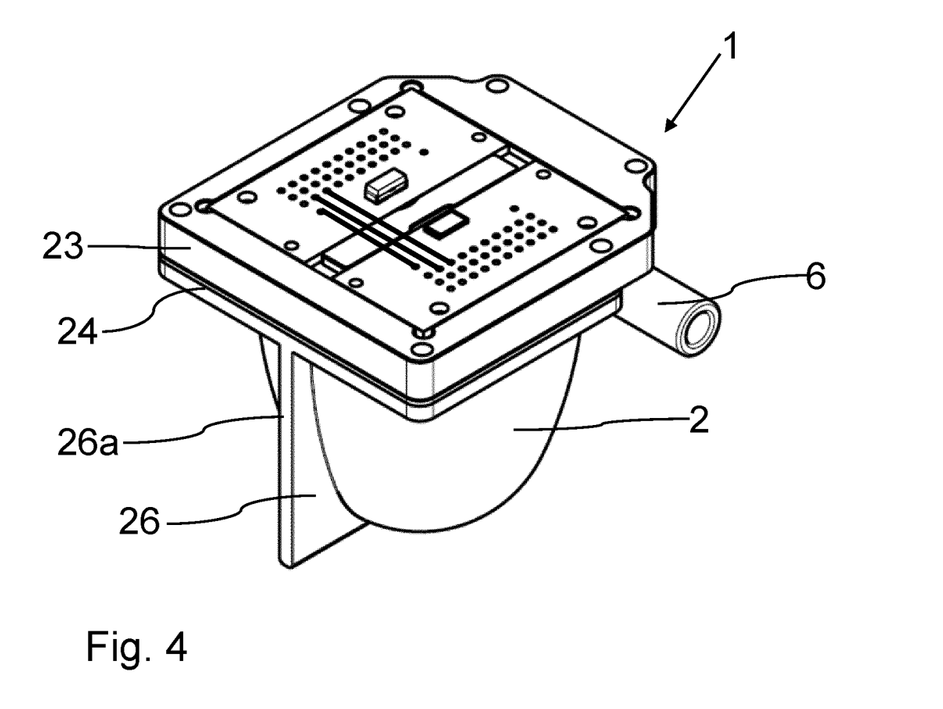
FIG. 4 shows a perspective view onto the lid of the container of the sensor shown in FIGS. 1 to 3.
Figure 5:
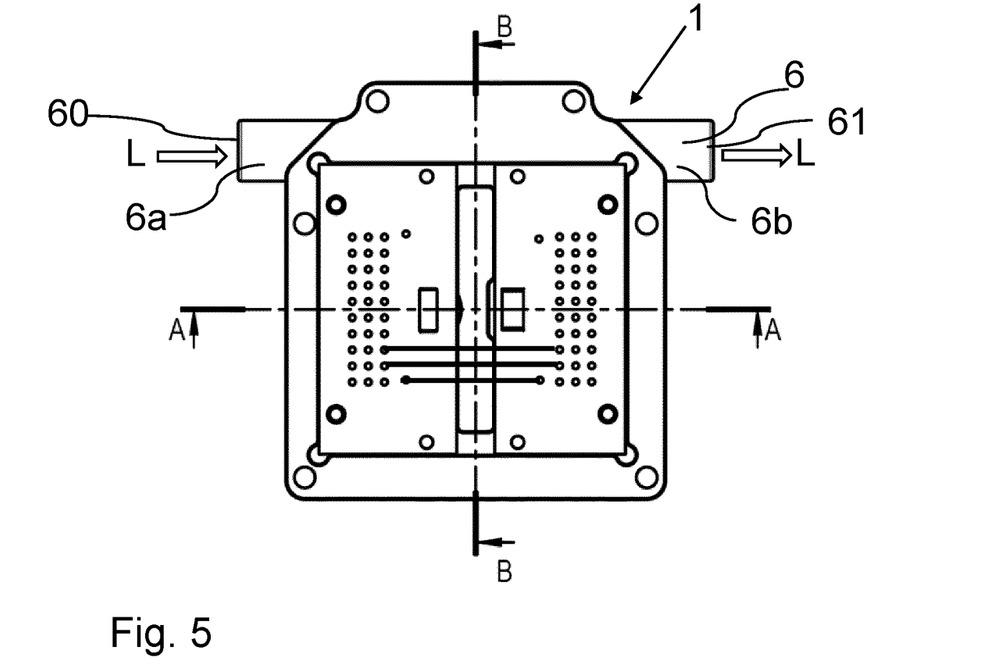
FIG. 5 shows a plan view onto the lid of the container of the sensor shown in FIGS. 1 to 4.

As e.g. shown in FIG. 2, the photodetector 3 is mounted to a first printed circuit board (PCB) 30, and the light source 4 is mounted to a second printed circuit board 40, wherein the two printed circuit boards 30, 40 are mounted to the lid 23. Alternatively, as e.g. shown in FIG. 9, the photodetector 3 and the light source 4 may also be arranged on the same printed circuit board 42. Thus, PCBs 30 and 40 may form a single PCB.

For the passage of light, the lid 23 comprises a first aperture 230 and a second aperture 231, wherein the photodetector 3 is arranged outside the interior space 20 of the container 2 in front of the first aperture 230 and the light source 4 is arranged outside the interior space 20 of the container 2 in front of the second aperture 231.

Particularly, the first aperture 230 is closed by a first optical window 31 allowing passage of light therethrough, wherein the first optical window 31 is configured to prevent liquid L residing inside the interior space 20 from leaking through the first aperture 230 out of the interior space 20. Furthermore, particularly, the second aperture 231 is closed by a second optical window 41 allowing passage of light therethrough, wherein the second optical window 41 is configured to prevent liquid L residing inside the interior space 20 from leaking through the second aperture 231 out of the interior space 20.

Particularly for maintaining or supporting a vertical orientation of the lid 23 or printed circuit boards 30, 40, the container 2 can comprise a protrusion 26 (cf. e.g. FIG. 1) protruding from an outside 28 of a wall 27 of the container 2, which wall 27 delimits the interior space 20 and comprises said interior surface 21, wherein said protrusion 26 comprises an edge 26a extending perpendicular to the lid 23 of the container 2. Thus, in case the sensor 1 rests with its edge 26a on a support, the lid 23 will extend perpendicular to the support.

In order to fill the interior space 20 of the container with a liquid L (e.g. water) to be tested, the sensor 1 comprises a conduit 6 (or channel) connected to the container 2. Particularly, the conduit 6 can be connected to the flange 25 of the container 2 and/or to an outside 28 of the wall 27 of the container 2 as e.g. shown in FIG. 2. As further indicated in FIG. 6 the conduit 6 can be formed by a tube comprising a lateral opening 61 that is in fluid communication with the interior space 20 of the container 2. Further, the tube or conduit 6 comprises an inlet 60 at one end 6a of the tube/conduit 6 and an outlet 62 at an opposing end 6b of the tube/conduit 6, so that liquid L can be passed into the interior space 20 of the container 2 via the inlet 60 and the lateral opening 61 and can be discharged out of the interior space 20 of the container 2 via the lateral opening 61 and the outlet 62 of the tube/conduit 6.

Figure 7:
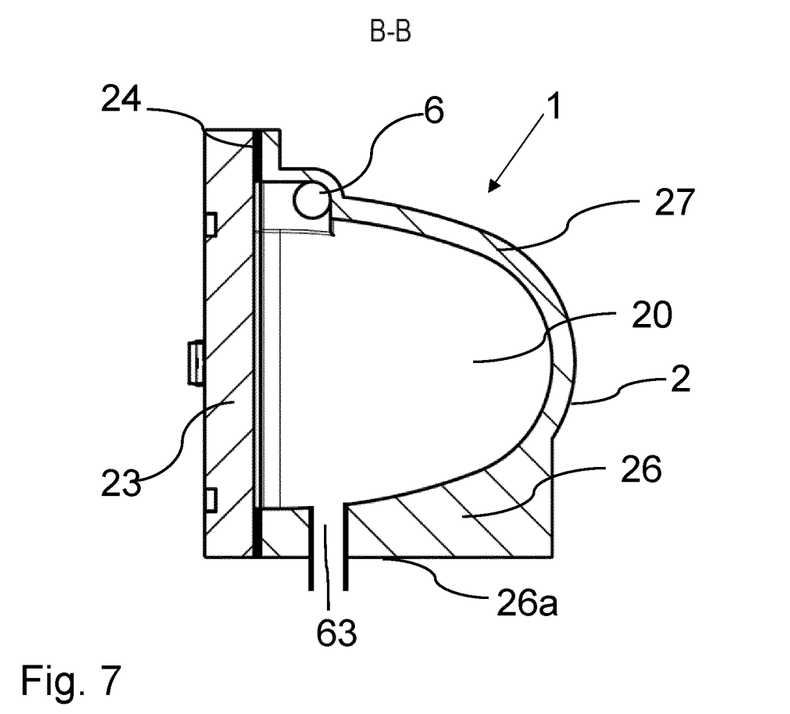
FIG. 7 shows a cross sectional view of the sensor shown in FIGS. 1 to 6 along the line B-B in FIG. 5.
Figure 8:
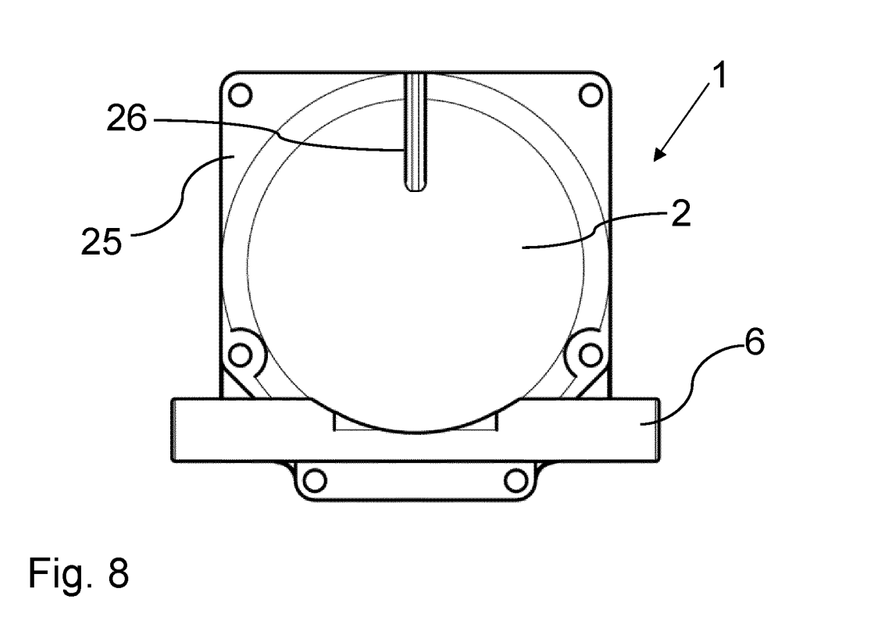
FIG. 8 shows a plan view onto a side of the container facing away from the lid of the sensor.

Furthermore, according to an embodiment, the sensor 1 can comprise an orifice 63 as shown in FIG. 7. The orifice 63 is only shown in FIG. 7 but can be present in all embodiments if needed. The orifice can be arranged in the wall 27 of the container 2. Particularly, the orifice 63 can be used to discharge liquid (e.g. water) from the interior space 20 of the container 2 of the sensor (e.g. into a water pipe) by which air can enter the interior space 20 of the container 2.

In order to analyze an output signal (e.g. electrical current) provided by the photodetector 3, the sensor 1 comprises an analyzing circuit 7 that generates an output of the sensor 1 from the photodetector's 3 output signal that is indicative of a concentration of organic carbon in said liquid L. Due to absorption of UV light by carbon bonds of organic molecules in the liquid L, the intensity of light finally impinging on the photodetector 3 changes accordingly which allows to determine the concentration of organic carbon, particularly TOC, in the liquid L in a known manner.

Preferably, the analyzing circuit 7 is integrated into the sensor 1. Particularly, the analyzing circuit 7 can be arranged on the first or the second printed circuit board 30, 40 (or on the printed circuit board in case a single printed circuit board is used). Most preferably, the analyzing circuit 7 is integrated on same chip as the photodetector 3 Alternatively, the analyzing circuit can also be arranged on an external component, e.g. in a water purifier, or in a mobile device such as a smartphone.

Figure 9:
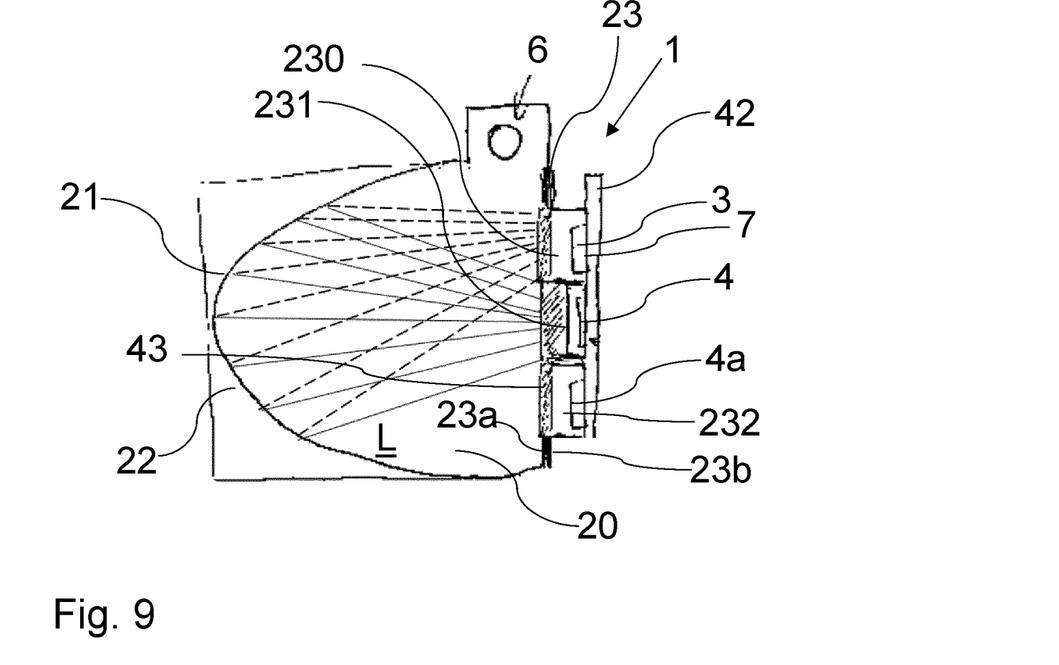
FIG. 9 shows a schematical cross sectional view of a further embodiment of the sensor according to the present invention.

According to an embodiment of the present invention shown in FIG. 9, the sensor 1 may comprise a further light source 4a configured to emit light in the visible spectrum such that the light is reflected by the down conversion material portion 22 of the interior surface 21 of the container 2. Here, the sensor 1 is configured to measure the light of the further light source 4a that is reflected by the interior surface 21 to estimate a value indicative of at least one of: an aging of the down conversion material portion 22 (due to ultraviolet light incident on the down conversion material portion 22, particularly photo bleaching of the down conversion material portion 22 due to ultraviolet light incident on the down conversion material portion 22), a contamination (e.g. scale, biofilm etc.) deposited on the down conversion material portion 22.

Particularly, the photodetector 3 can also be used to measure said reflected visible light coming from the further light source 4a. Alternatively, the sensor 1 may comprise a further photodetector (e.g. a photodiode sensing in a visible spectrum) to measure the visible light coming from the further light source 4a and reflected from the interior surface 21 of the interior space 20 of the container 2. Furthermore, as indicated in FIG. 9, the further light source 4a can be arranged on the same printed circuit board 42 as the photodetector 3 and the light source 4. Preferably, the further light source 4a is arranged adjacent the light source 4 that emits the absorbable ultraviolet light 5 and can be covered by an optical window 43 sealing a corresponding aperture 232 of the lid 23 in front of which the further light source 4a is arranged.

Particularly, the analyzing circuit 7 is configured to use said estimated value in the generation of said sensor output to compensate an effect of at least one of said aging (e.g. bleaching) and contamination. Furthermore, the analyzing circuit 7 can also be configured to use the visible light source to compensate for turbidity in the liquid L. Particularly, the liquid L can be measured/analyzed while flowing through the interior space 20 of the container 2 or while resting inside said interior space 20 of the container 2.

Figure 10:
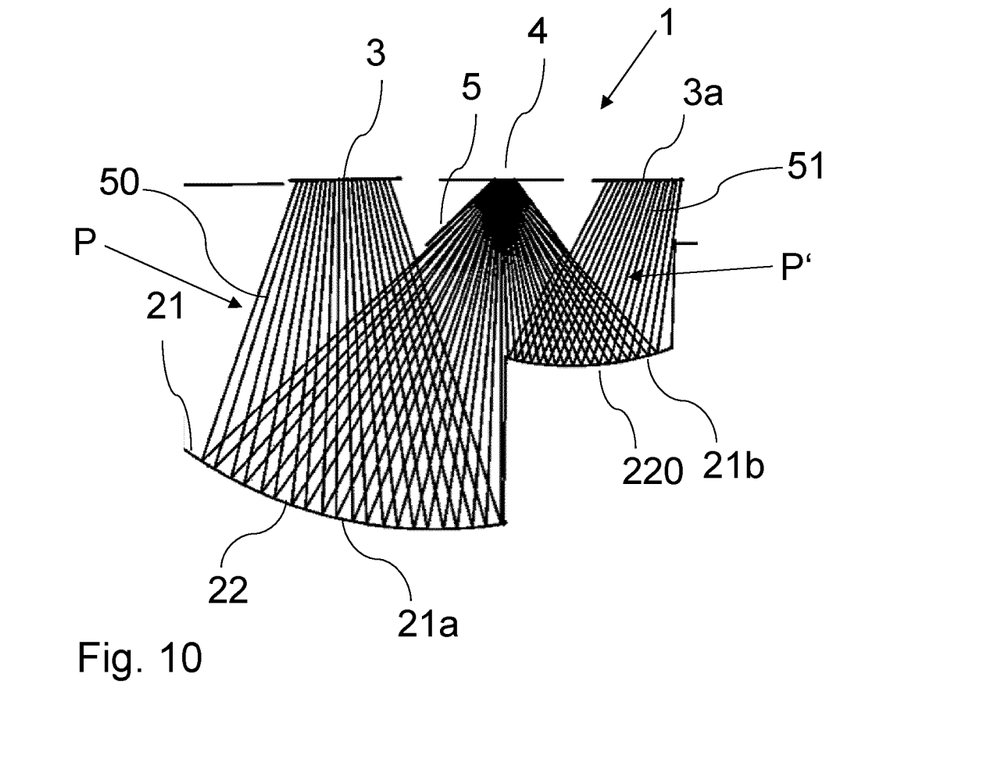
FIG. 10 shows a schematical illustration of a further embodiment of a sensor according to the present invention.

In order to correct for aging (particularly bleaching) or contamination, the sensor 1 may also comprise a further photodetector 3a according to the embodiment shown in FIG. 10. Here, the further photodetector 3a is also configured to detect light in the visible or infrared spectrum. Using two photodetectors 3, 3a, in addition to the optical path P described above, the light source 4 is further configured to also emit ultraviolet light 5 that travels along a further optical path P' through the liquid L and is absorbable by carbon bonds of organic molecules in the liquid L, wherein a further down conversion material portion 220 is arranged in the further optical path P' and down converts received ultraviolet light 5 and correspondingly emits down converted light 51 in the visible or infrared spectrum so that such emitted down converted light 51 impinges on the further photodetector 3a. Due to the fact that the lengths of the optical paths P and P' are selected to differ from one another the output signals of the photodetectors 3, 3a can be used to compensate aging (e.g. bleaching or contamination of the down conversion material portions 22, 220 and other parts of the sensor 1 such as the optical windows 31, 41.

For this, the analyzing circuit 7 can e.g. be configured to form a quotient of the output signals of the photodetectors 3, 3a or a quotient of quantities derived from these output signals.

Particularly, according to FIG. 10, the interior surface 21 comprises a first curved (e.g. concave or parabolic) region 21a and a curved second (e.g. concave or parabolic) region 21b, wherein the first region 21a is formed by the down conversion material portion 22 and the second region 21b is formed by the further down conversion material portion 220 (said portions 22, 220 are preferably made from the same down conversion material), such that ultraviolet light 5 traveling along the optical path P impinges on the first region 21a of the interior surface 22 and down converted light 50 emitted by said first region 21a of the interior surface 21 impinges on the photodetector 3, and such that ultraviolet light 5 traveling along the further optical path P' impinges on the second region 21b of the interior surface 21 and down converted light 51 emitted by said second region 21b of the interior surface 21 impinges on the further photodetector 3a.

Figure 11:
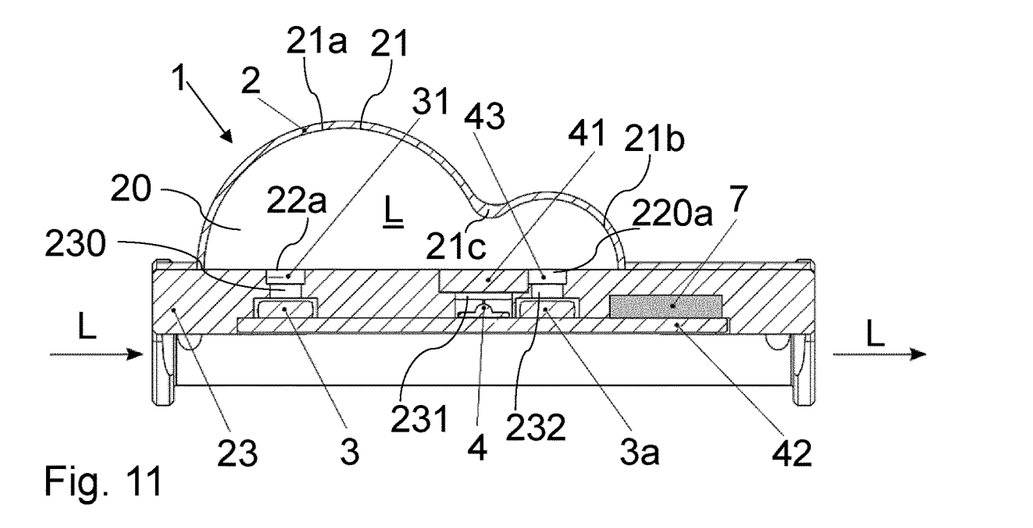
FIG. 11 shows a schematical illustration of a further embodiment of a sensor according to the present invention.
Figure 12:
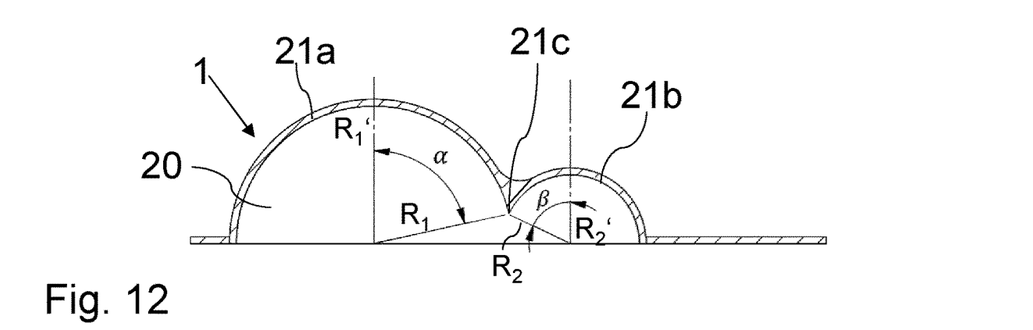
FIG. 12 shows the shape of the first and second region of the interior surface of the container of the sensor of FIG. 11.
Figure 13:
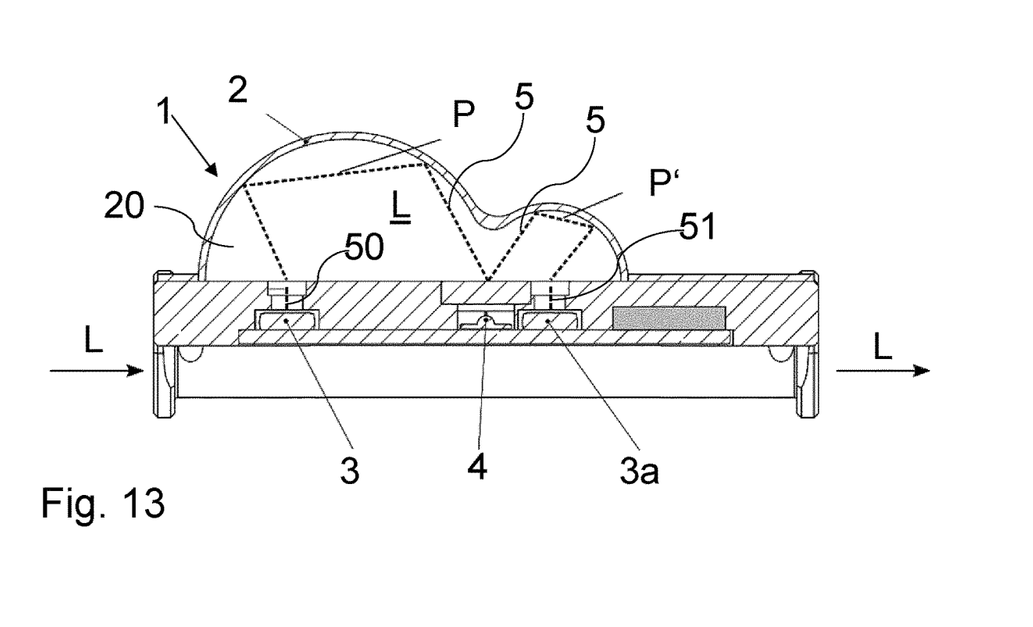
FIG. 13 shows two possible optical paths from the light source to the respective photodetector of the sensor of FIG. 11.

Furthermore, FIGS. 11 to 13 show a further embodiment of a sensor 1 according to the present invention using to photodetectors 3, 3a and a light source 4 arranged between the photodetectors 3, 3a.

Also here, the interior surface 21 of the container 2 of the sensor 1 comprises a first curved (e.g. hemispherical) region 21a and a curved second (e.g. hemispherical) region 21b, wherein the first region 21a and the second region 21b each form an optical diffuser configured to reflect incident UV light from the light source 4 in a diffuse manner.

As indicated in FIGS. 11 to 13, two down conversion material portions 22a, 220a are placed in the optical paths P, P' (cf. FIG. 13) between the liquid L (e.g. water) and the photodetectors 3, 3a. As e.g. described above, liquid L to be analyzed can be passed through the interior space 20 of the container 2. Preferably, the photodetector 3 is separated from the interior space 20 of the container 2 of the sensor 1 by a first optical window 31, that can be arranged in a first aperture 230 of a lid 23 or wall 23 closing the interior space 20/container 2. Furthermore, preferably, the further photodetector 3 is separated from the interior space 20 of the container 2 of the sensor 1 by a second optical window 43, that can be arranged in a second aperture 232 of said lid or wall 23. The light source can be separated from said interior space 20/container 2 by a third optical window 42 that can be arranged in a third aperture 231 of said lid or wall 23. Particularly, the photodetectors 3, 3a and the UV light source 4 are arranged on a printed circuit board 42 that is connected to said lid or wall 23, wherein the photodetectors 3, 3a and the light source 4 are arranged in the associated aperture 230, 232, 231.

Thus, ultraviolet light 5 traveling along the optical path P impinges on the first region 21a of the interior surface 22, is reflected in a diffuse manner, impinges on the down conversion material portion 22a comprised or formed by the first optical window 31 and down converted light 50 is emitted by said down conversion material portion 22a and impinges on the photodetector 3. In the same fashion, ultraviolet light 5 traveling along the further optical path P' impinges on the second region 21b of the interior surface 21 undergoes diffuse reflection and impinges on the further down conversion material portion 220a comprised or formed by the second optical window 43, wherein down converted light 51 emitted by said further down conversion material portion 220a impinges on the further photodetector 3a. In this way, the sensor 1 can work in differential mode.

Particularly, as indicated in FIG. 12, the two curved regions 21a, 21b of the interior surface 21 of the container can be hemispheres 21a, 21b that are meeting one another at an intersection 21c such that for each of the two hemispheres 21a, 21b, the radius $R_1$, $R_2$ pointing to the intersection 21c and the radius $R_1'$, $R_2'$ pointing to the apex of the respective region 21a, 21b form an angle α (region 21a) or β (region 21b), wherein the respective angle α, β is in the range between 0° and 90°. The two regions 21a, 21b of the interior surface 21 are configured to allow diffuse reflection of the incoming light 5. Particularly, the regions 21a, 21b can each have a reflectance in the range from 0.1 to 0.99.

Furthermore, preferably, the UV light source 4 is aligned with the intersection 21c where the two curved (hemispherical) regions 21a, 21b meet/intersect with each other. The light 5 emitted from the UV light source 4 is traveling through the liquid (e.g. water) L in the two cavities adjacent the respective region 21a, 21b of the interior surface 21 and absorbed by the organic molecules therein. The light 5 is directed to said diffuser regions 21, 21b independently. The geometry of the two diffusive regions 21a, 21b of the interior surface 21 and the positions of the photodetectors 3, 3a and the UV light source 4 are configured such that the light 5 impinging on the windows 31, 43 (which light 5 is down-converted by the windows 31, 43 and emitted as down-converted light 50, 51 that eventually impinges on the respective photodetector 3, 3a) is mostly diffuse reflected light. Said diffuse reflected light 5 coming from the diffusers 21a, 21b is traveling through water and absorbable by organic molecules. The sensor 1 is configured such that the ratio between light intensity on the two photodetectors 3, 3a is constant for any reflectance of the regions 21a, 21b of the interior surface 21. The ratio is nevertheless a function of the TOC content in the liquid/water L.

Using the down converting optical windows 31, 43 makes the use of the two photodetectors possible that detect visible/IR light. However, it is also possible to omit the down conversion material portion(s) and to use UV photodetectors instead.

Each of the optical windows 31, 43 separating the respective photodetector 3, 3a from the interior space/cavity 20 containing the liquid (e.g. water) collects the UV light 5 from the source 4 after being absorbed by organic molecules in the liquid L and re-emits down-converted light 50, 51 to impinge on one of the two photodetectors 3, 3a. For this reason, said optical windows 31, 43 are made of a down conversion material such as ruby. However, other materials disclosed herein can also be used. Preferably, the two curved regions 21a, 21b of the interior surface 21 are configured to direct specular reflections of the light emitted from the UV source 4 away from the down-converting optical windows 31, 43. The regions 21a, 21b are preferably configured such that mainly diffuse reflected light is impinging on the down-converting optical windows 31, 43. This helps to achieve that the ratio of the signals coming from the two photodetectors 3, 3a is constant regardless of the optical properties of the interior surface 21, i.e. of the regions 21a, 21b.

The invention claimed is:

1. A sensor (1) for sensing carbon bonds of organic molecules in a liquid (L), comprising:
a container (2) having an interior space (20) for receiving the liquid (L),
a photodetector (3), and
a light source (4) configured to emit ultraviolet light (5) so that the ultraviolet light (5) travels along an optical path (P) through liquid (L) residing in the interior space (20) and is absorbable by carbon bonds of organic molecules in the liquid (L),
wherein
the photodetector (3) is configured to detect light in the visible or infrared spectrum, and the sensor (1) comprises a down conversion material portion (22; 22a) arranged in the optical path (P), wherein the down conversion material portion (22; 22a) is configured to receive incoming ultraviolet light (5) emitted by the light source (4) and to down convert received ultraviolet light (5) and to emit said down converted light (50) in the visible or infrared spectrum so that emitted down converted light (50) impinges on the photodetector (3), and wherein the down conversion material portion comprises a fluorescent mineral.

2. The sensor according to claim 1, wherein the container (2) comprises an interior surface (21) facing the interior space (20) of the container (2).

3. The sensor according to claim 2, wherein the interior surface (21) comprises one of: a flat region, a curved region, a concave region, a parabolic region, an ellipsoidal region.

4. The sensor according to claim 2, wherein at least a region of said interior surface (21) is formed by said down conversion material portion (22).

5. The sensor according to claim 2, wherein the sensor (1) comprises a further light source (4a) configured to emit light in the visible spectrum such that the light is reflected by the down conversion material portion (22) of the interior surface (21) of the container (2), wherein the sensor (1) is configured to measure the reflected light to estimate a value indicative of at least one of: an aging of the down conversion material portion (22), a contamination deposited on the down conversion material portion (22).

6. The sensor according to claim 2, wherein the interior surface (21) comprises a first region (21a) and a second region (21b).

7. The sensor according to claim 6, wherein the first region (21a) of the interior surface (21) is one of: a curved region, a concave region, a parabolic region, an ellipsoidal region, a hemispherical region; and/or wherein the second region (21b) of the interior surface (21) is one of: a curved region, a concave region, a parabolic region, an ellipsoidal region, a hemispherical region.

8. The sensor according to claim 6, wherein the first region (21a) of the interior surface comprises a curvature having a radius that is larger than a radius of a curvature of the second region (21b) of the interior surface (21).

9. The sensor according to claim 6, wherein the first and the second region (21a, 21b) of the interior surface (21), meet at an intersection (21c) such that for each of the two regions (21a, 21b), a radius ($R_1$, $R_2$) pointing to the intersection (21c) and a radius ($R_1$, $R_2$) pointing to the apex of the respective region (21a, 21b) form an angle (α, β) between 0° and 90°.

10. The sensor according to claim 1, wherein said down conversion material portion forms (22a) a layer (22a) arranged on the photodetector (3).

11. The sensor according to claim 1, wherein the down conversion material portion comprises one or more of the following additives: an ultraviolet absorbers, rutile titanium oxide, titan dioxide, hydroxybenzophenone, hydroxybenzophenone oxanilide, hydroxyphenylbenzotriazole, hydroxyphenylbenzotriazole oxanilide, benzophenone, benzotriazole, hydroxyphenyltriazine, a quencher, a nickel quencher, a hindered amine light stabilizer (HALS), 2,2,6,6-tetramethylpiperidine.

12. The sensor according to claim 1, wherein the sensor (1) comprises a lid (23) connected to the container (2) for closing the container (2).

13. The sensor according claim 12, wherein the photodetector (3) and the light source (4) are mounted to the lid (23).

14. The sensor according to claim 12, wherein the photodetector (3) and the light source (4) are arranged on a printed circuit board that is mounted to the lid (23), or wherein the photodetector (3) is mounted to a first printed circuit board (30) and the light source (4) is mounted to a second printed circuit board (40), wherein the two printed circuit boards (30, 40) are mounted to the lid (23).

15. The sensor according to claim 12, wherein the lid (23) comprises a first aperture (230) to allow passage of light from the interior space (20) towards the photodetector (3), and wherein the lid (23) comprises a second aperture (231) to allow passage of ultraviolet light (5) emitted by the light source (4) into the interior space of the container (20).

16. The sensor according to claim 1, wherein the sensor (1) comprises a conduit (6) connected to the container (2) configured to guide liquid (L) into the interior space (20) of the container (2) and out of the interior space (20) of the container (2), wherein the conduit (6) is connected to a boundary portion of the container (2) comprising an opening (2b) of the container (2) that is closed by the lid (23).

17. The sensor according to claim 1, wherein the sensor (1) comprises an analyzing circuit (7) configured to analyze an output signal of the photodetector (3) and to generate an output indicative of a concentration of organic carbon in said liquid (L).

18. The sensor according to claim 1, wherein the sensor (1) comprises a further photodetector (3a) configured to detect light in the visible or infrared spectrum, and wherein the light source (4) is further configured to also emit ultraviolet light that travels along a further optical path (P') through the liquid (L) and is absorbable by carbon bonds of organic molecules in the liquid (L), wherein the sensor (1) comprises a further down conversion material portion (220) arranged in the further optical path (P'), wherein the further down conversion material portion (220) is configured to receive incoming ultraviolet light emitted by the light source (4) and to down convert received ultraviolet light and to emit said down converted light (51) in the visible or infrared spectrum so that emitted down converted light (51) impinges on the further photodetector (3a), and wherein a length of the optical path (P) differs from a length of the further optical path (P').

19. The sensor according to claim 18, wherein the sensor (1) comprises a first optical window (31) separating the photodetector (3) from the interior space (20) of the container, and wherein the sensor (1) comprises a second optical window (43) separating the further photodetector (3a) from the interior space (20) of the container (2).

20. The sensor according to claim 19, wherein the down conversion material portion (22a) is comprised or formed by the first optical window (31), and wherein the further down conversion material portion (220a) is comprised or formed by the second optical window (43).

21. The sensor according to claim 18, wherein the further down conversion material portion (220a) comprise or are formed out of one of the following materials: a fluorescent mineral, ruby, willemite, fluorite, calcite, agrellite, apatite, aragonite, baryte, cerussite, chalcedony, corundum, esperite, hardystonite, hyalite, hydrozincite, opal, pyromorphite, scapolite, scheelite, selenite, smithsonite, sodalite, sphalerite, tremolite, tugtupite, wollastonite, caliche.

22. The sensor according to claim 18, wherein the container (2) comprises an interior surface (21) facing the interior space (20) of the container (2), and wherein the photodetector (3) faces a first region (21a) of the interior surface (21), and wherein the further photodetector (3a) faces a second region (21b) of the interior surface (21), and wherein the light source (4) faces an intersection (21c) at which the first and the second region (21, 21b) meet.

23. The sensor according to claim 22, wherein the first region (21a) and the second region (21b) of the interior surface (21) are each configured to reflect incoming light in a diffuse manner and each comprise a reflectance between 0.1 and 0.99.

24. The sensor according to claim 22, wherein the first and the second region (21a, 21b) of the interior surface (21) are configured to direct specular reflections of light emitted by the light source away from the first and second optical window (31, 43), wherein particularly, the first and the second region (21a, 21b) of the interior surface (21) are configured such that mainly diffuse reflected light is impinging on said two optical windows (31, 43).

25. The sensor according to claim 22, wherein the photodetector (3) and the further photodetector (3a) are each configured to generate an output signal indicative of an intensity of the light impinging on the respective photodetector (3, 3a), wherein a ratio of the two output signals is indicative of a concentration of organic carbon in said liquid (L) and independent of the total reflectance and the proportion between specular reflectance and diffuse reflectance of the first and second region (21a, 21b) of the interior surface (21).

26. The sensor according to claim 1, wherein the fluorescent mineral is ruby.

\* \* \* \* \*